United States Patent
Shaw

(10) Patent No.: US 8,343,094 B2
(45) Date of Patent: Jan. 1, 2013

(54) UNIVERSAL SYRINGE WITH RETRACTABLE NEEDLE

(76) Inventor: Thomas J. Shaw, Frisco, TX (US)

( * ) Notice: Subject to any disclaimer, the term of this patent is extended or adjusted under 35 U.S.C. 154(b) by 0 days.

(21) Appl. No.: 12/837,228

(22) Filed: Jul. 15, 2010

(65) Prior Publication Data

US 2010/0286604 A1    Nov. 11, 2010

Related U.S. Application Data

(63) Continuation of application No. PCT/US2009/059962, filed on Oct. 8, 2009.

(60) Provisional application No. 61/107,578, filed on Oct. 22, 2008.

(51) Int. Cl.
*A61M 5/30* (2006.01)

(52) U.S. Cl. ......................................... 604/68

(58) Field of Classification Search ................ 604/68
See application file for complete search history.

(56) References Cited

U.S. PATENT DOCUMENTS

| | | | |
|---|---|---|---|
| 1,668,315 A | 5/1928 | Hein | |
| 2,158,593 A | 5/1939 | Scrimgeour | |
| 4,123,091 A | 10/1978 | Cosentino et al. | |
| 4,326,569 A | 4/1982 | Vaillancourt | |
| 4,490,142 A | 12/1984 | Silvern | |
| 4,718,463 A | 1/1988 | Jurgens, Jr. et al. | |
| 4,743,233 A | 5/1988 | Schneider | |
| 4,747,835 A | 5/1988 | Sandhaus | |
| 4,838,869 A | 6/1989 | Allard | |
| 5,205,833 A | 4/1993 | Harsh et al. | |
| 5,322,515 A * | 6/1994 | Karas et al. | 604/192 |
| 5,419,775 A | 5/1995 | Haffner et al. | |
| 5,531,699 A | 7/1996 | Tomba et al. | |
| 5,573,516 A * | 11/1996 | Tyner | 604/249 |
| 5,616,136 A | 4/1997 | Shillington et al. | |
| 5,694,686 A | 12/1997 | Lopez | |
| 5,702,367 A | 12/1997 | Cover et al. | |
| 5,807,343 A | 9/1998 | Tucker et al. | |
| 5,827,244 A | 10/1998 | Boettger | |
| 5,902,271 A | 5/1999 | Jentzen | |
| 5,919,169 A | 7/1999 | Grams et al. | |
| 5,980,495 A | 11/1999 | Heinz et al. | |
| 6,068,614 A | 5/2000 | Kimber et al. | |
| 6,090,077 A * | 7/2000 | Shaw | 604/195 |
| 6,126,640 A | 10/2000 | Tucker et al. | |
| 6,217,550 B1 | 4/2001 | Capes | |
| 6,382,204 B1 | 5/2002 | Jansen et al. | |
| 6,517,516 B1 * | 2/2003 | Caizza | 604/110 |
| 6,544,233 B1 | 4/2003 | Fukui et al. | |
| 6,740,060 B2 | 5/2004 | Tanaka et al. | |
| 6,758,833 B2 | 7/2004 | Lopez | |

(Continued)

FOREIGN PATENT DOCUMENTS

| | | |
|---|---|---|
| JP | 6181985 | 7/1994 |
| JP | 20021722166 | 6/2002 |
| WO | WO 93/11828 | 6/1993 |
| WO | WO 94/13345 | 6/1994 |
| WO | WO 2005/006567 | 7/2005 |

*Primary Examiner* — Nicholas Lucchesi
*Assistant Examiner* — Jason Flick
(74) *Attorney, Agent, or Firm* — Monty L Ross; Robin L Barnes; Ross Barnes LLP

(57) ABSTRACT

This invention relates to medical devices useful for infusion therapy and, more particularly, to a syringe that can be selectively used with a retractable needle or with frontal attachment devices such as luer hubs, valves or other connectors in needleless systems.

2 Claims, 9 Drawing Sheets

U.S. PATENT DOCUMENTS

| | | |
|---|---|---|
| 2002/0004648 A1 | 1/2002 | Larsen et al. |
| 2003/0149403 A1 | 8/2003 | Barker et al. |
| 2003/0199847 A1 | 10/2003 | Akerlund et al. |
| 2004/0087906 A1 | 5/2004 | Henderson et al. |
| 2007/0260189 A1 | 11/2007 | Shaw et al. |
| 2008/0132851 A1 | 6/2008 | Shaw et al. |

* cited by examiner

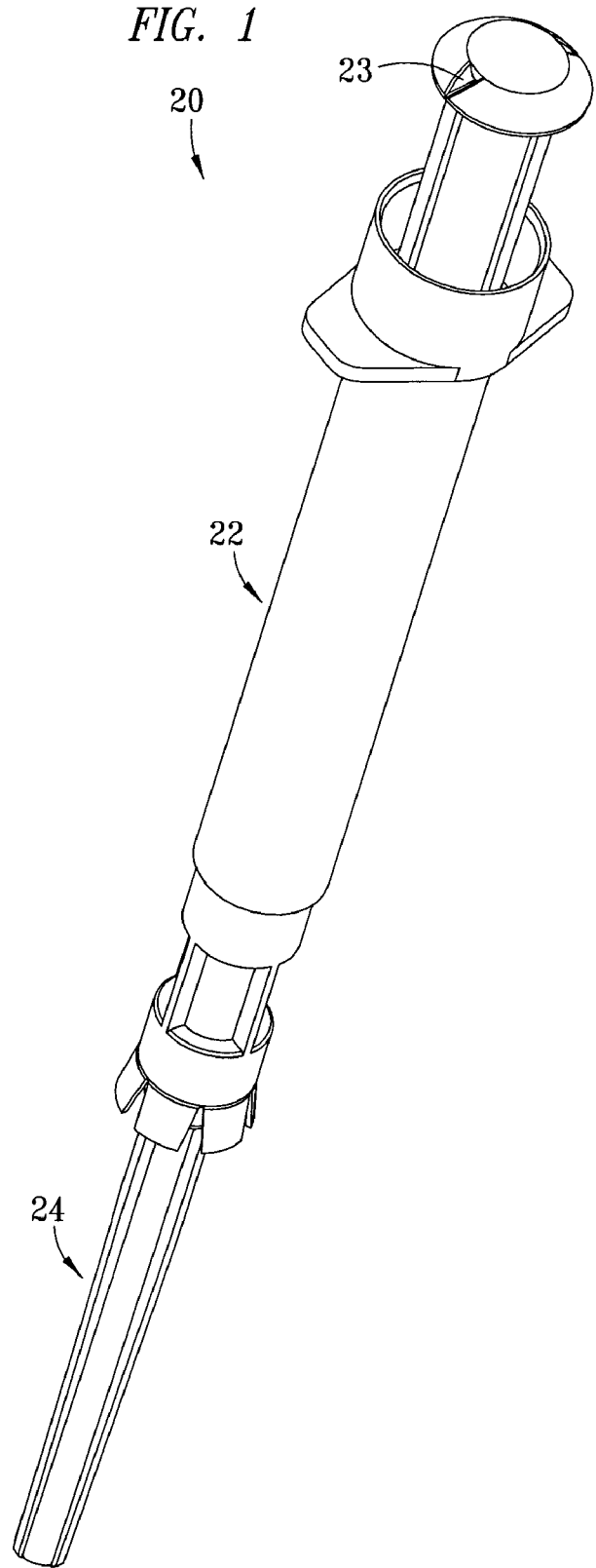

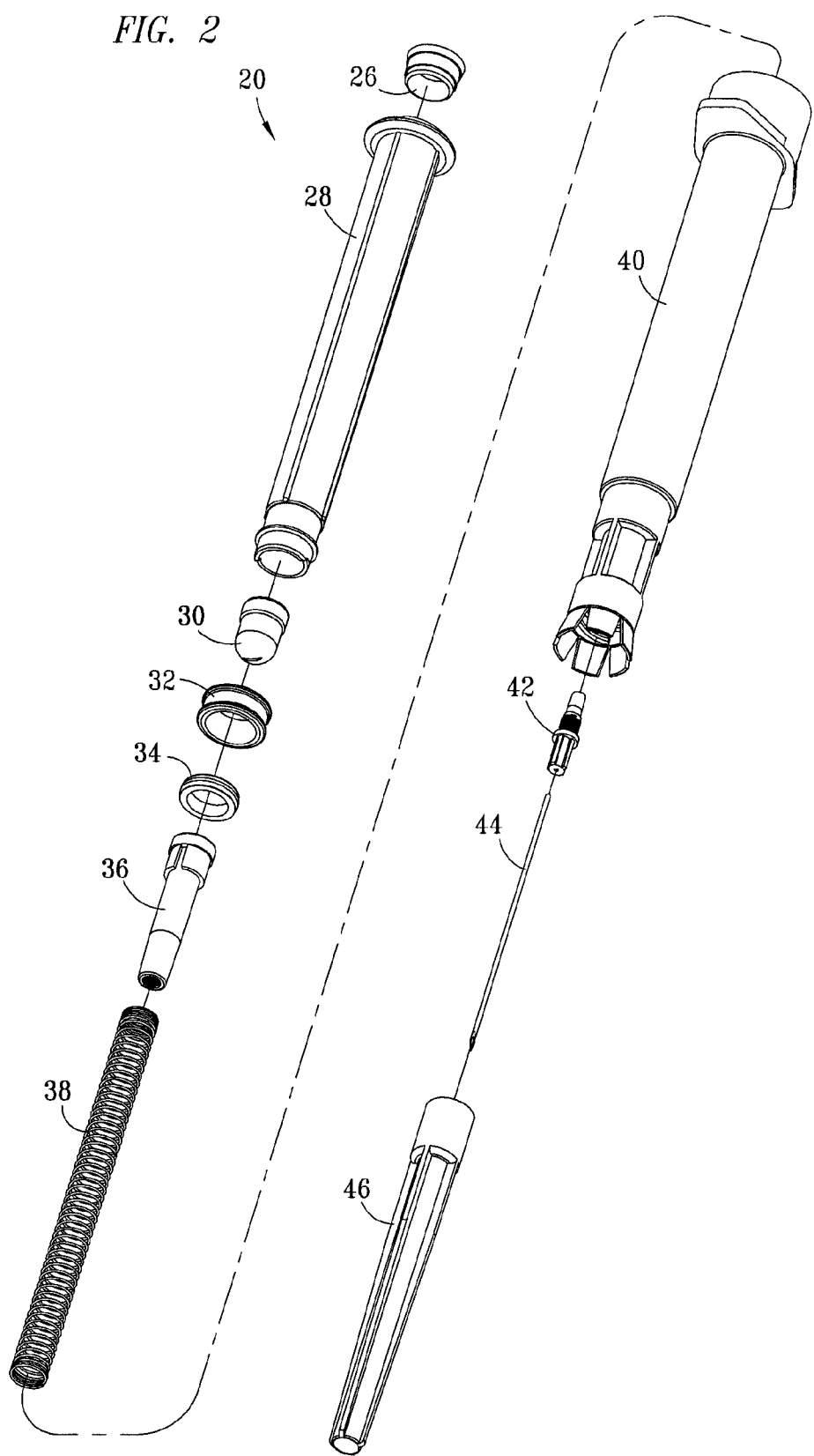

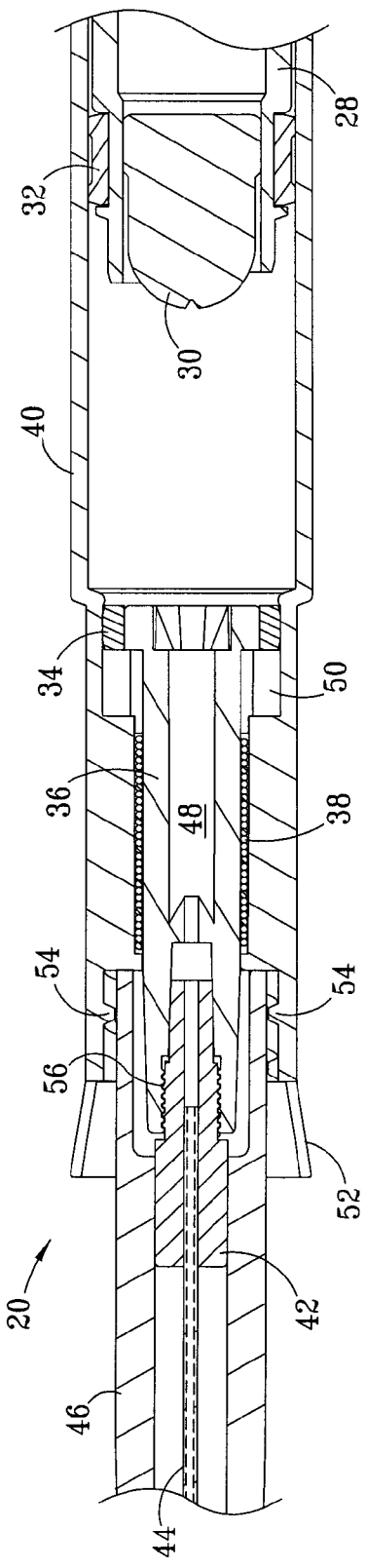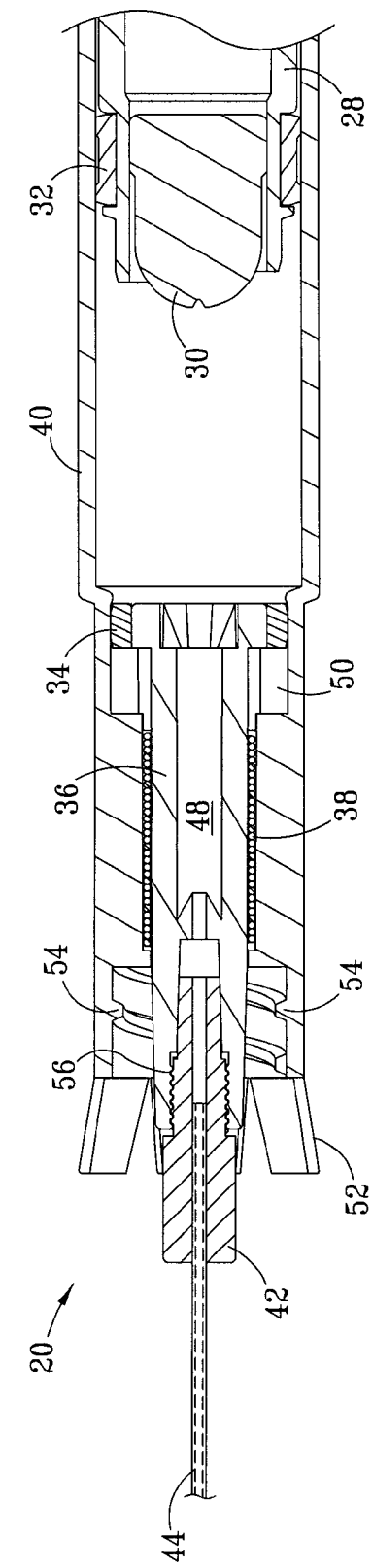

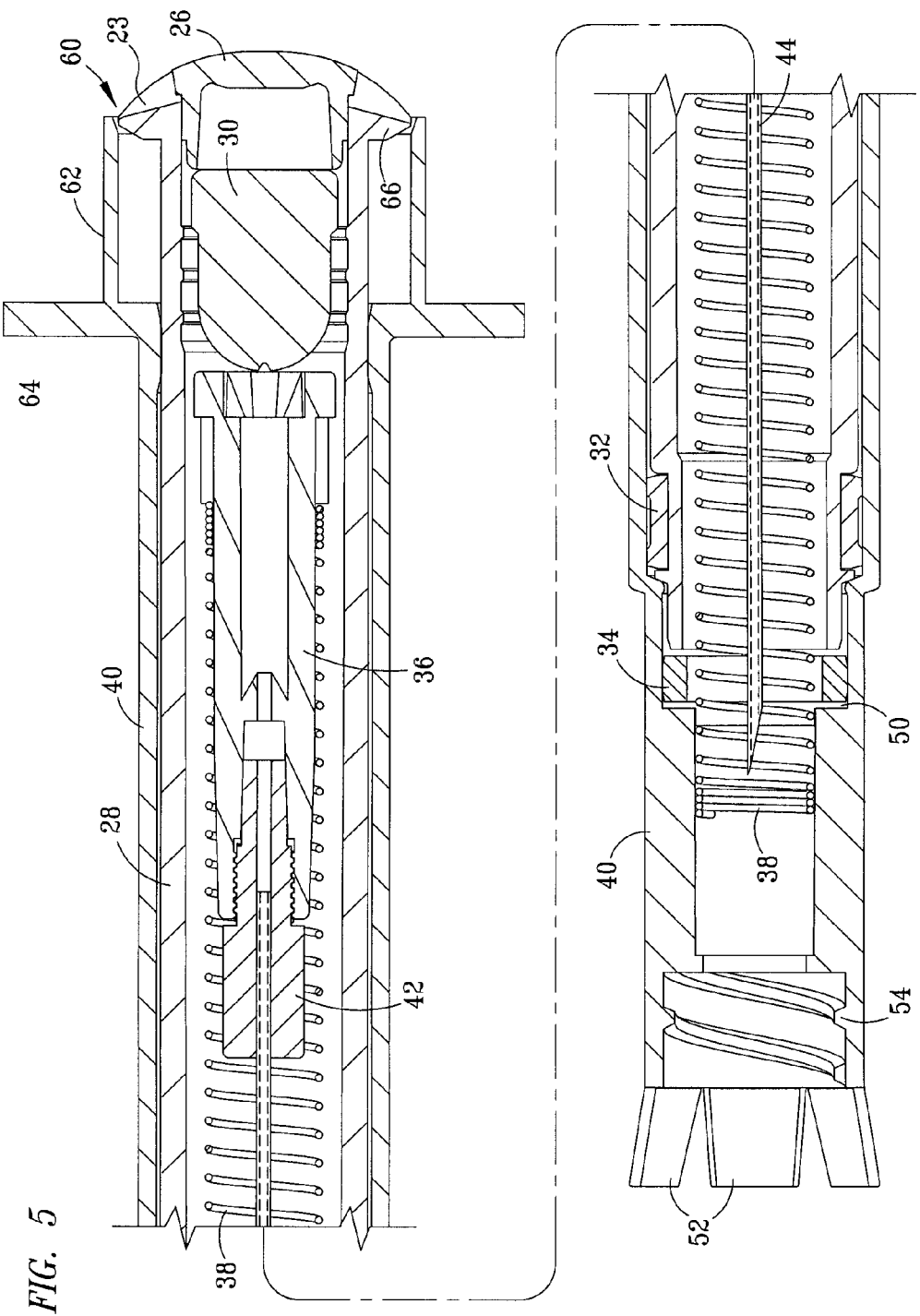

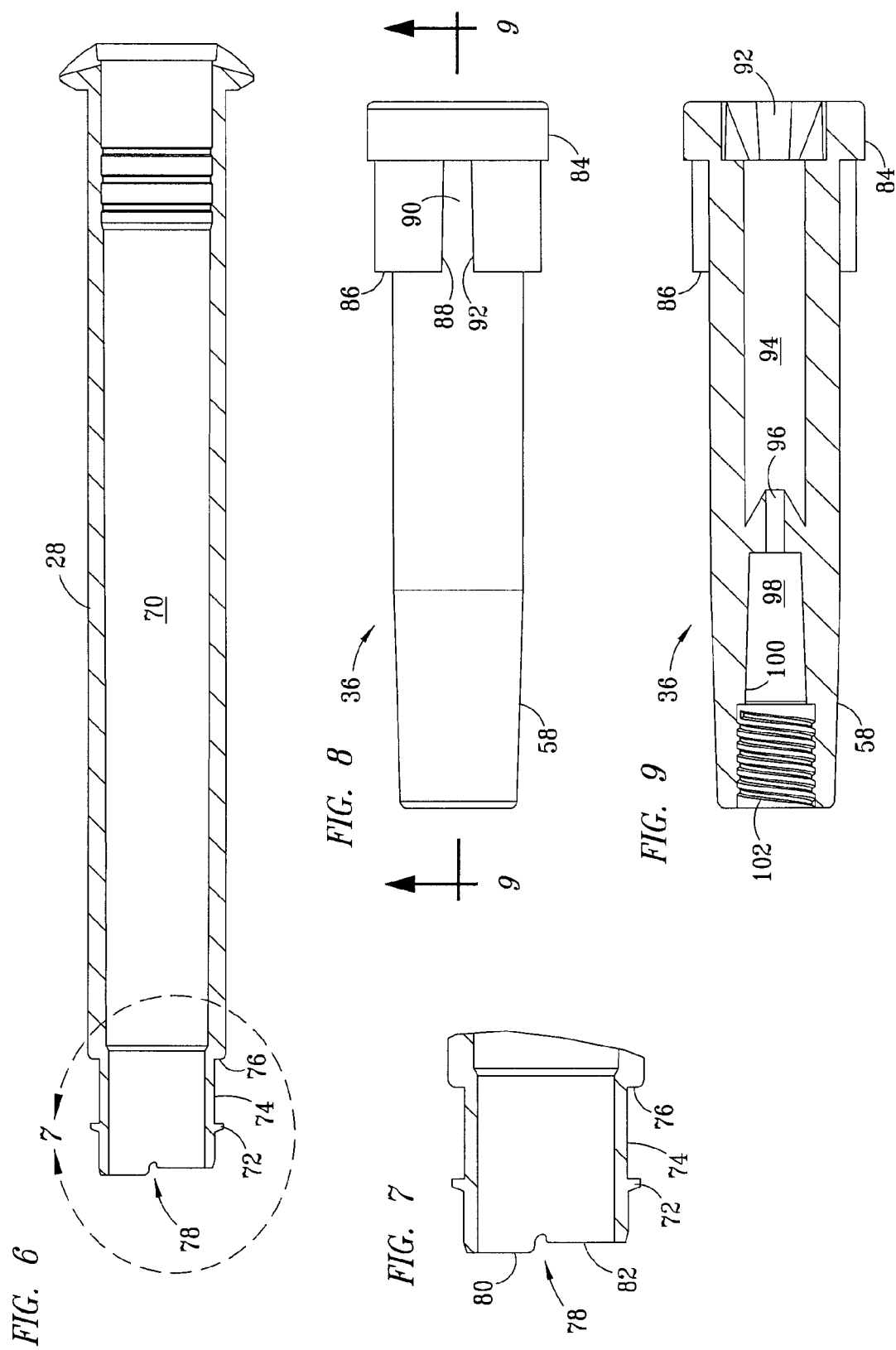

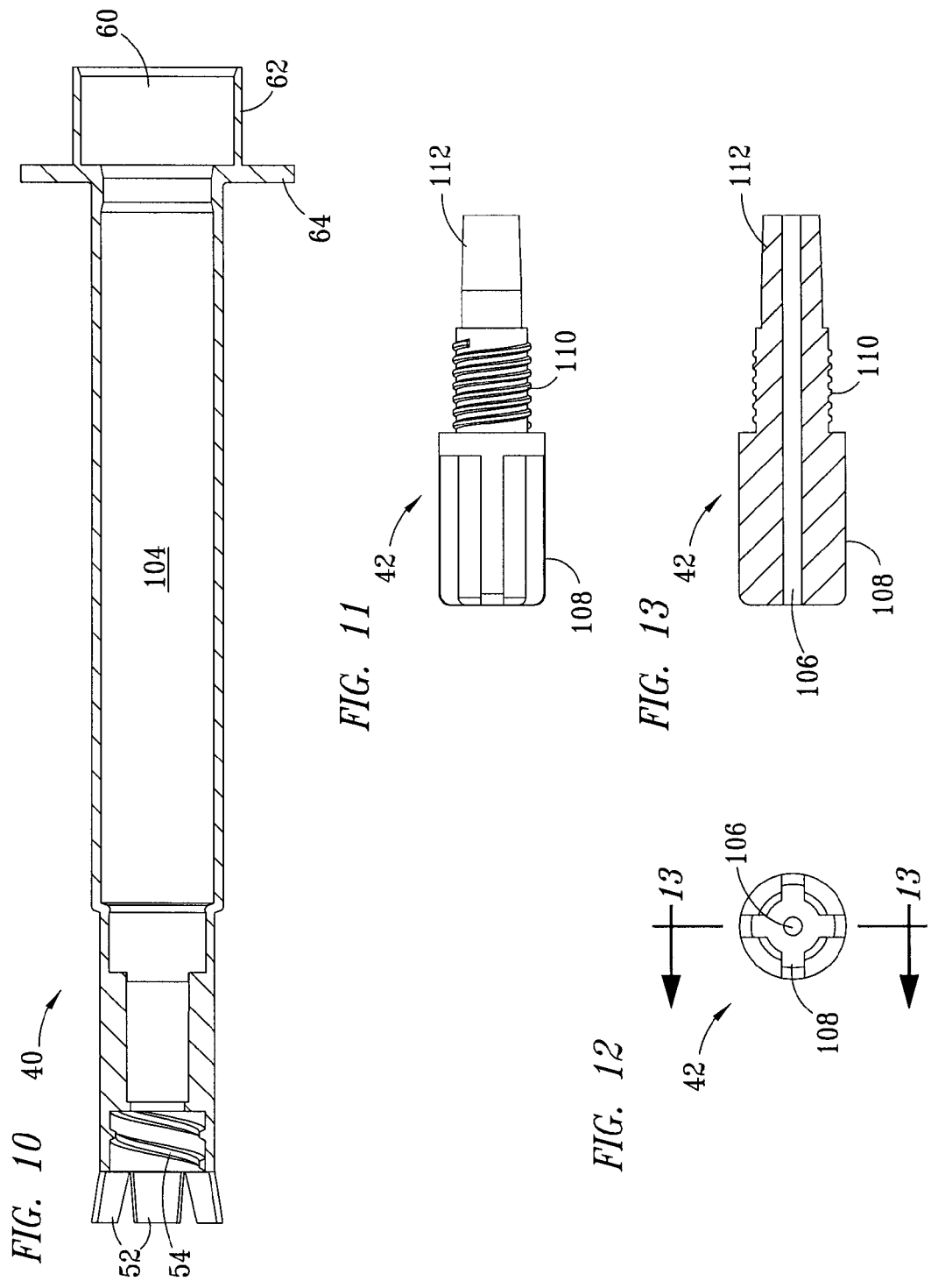

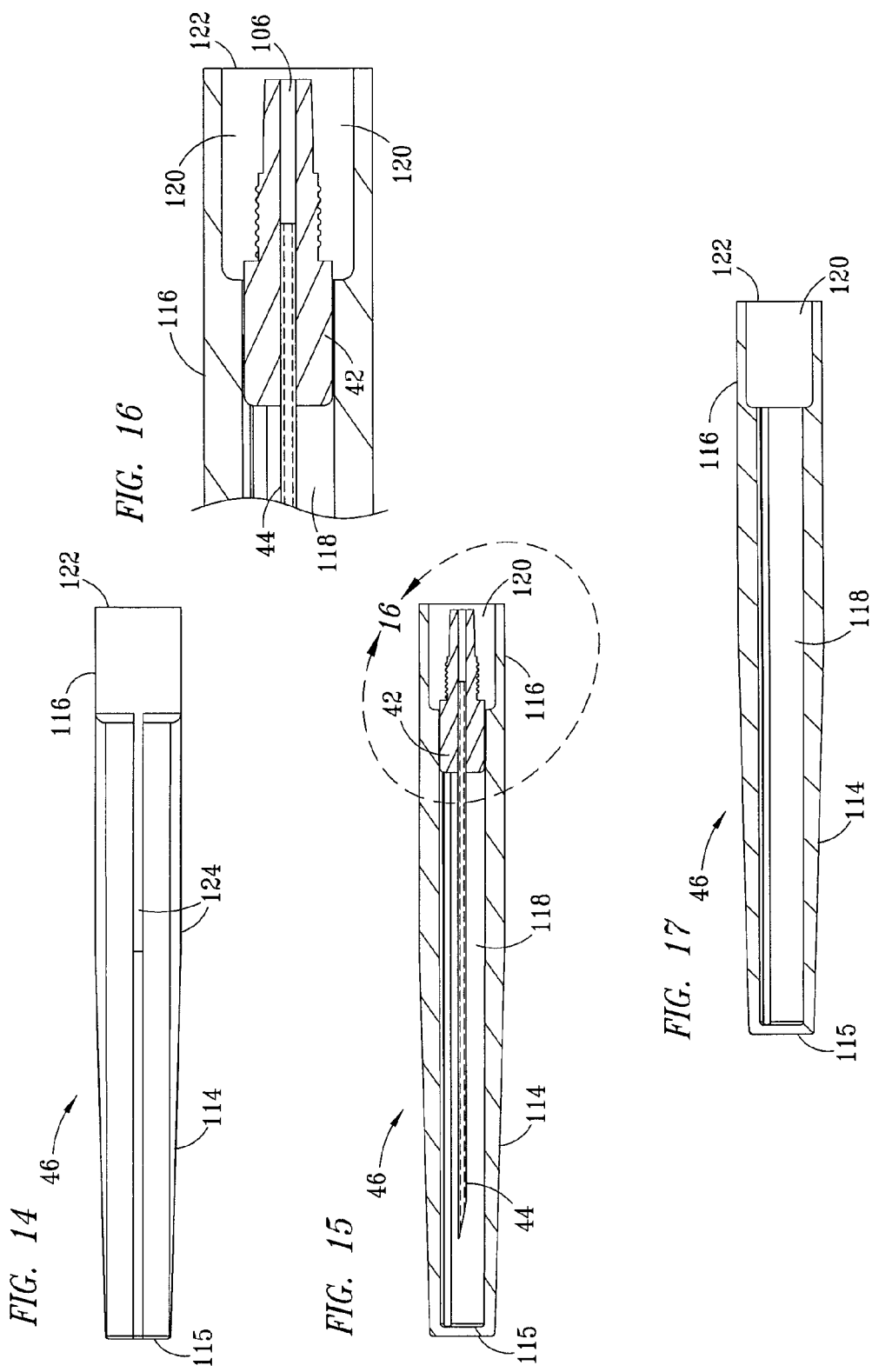

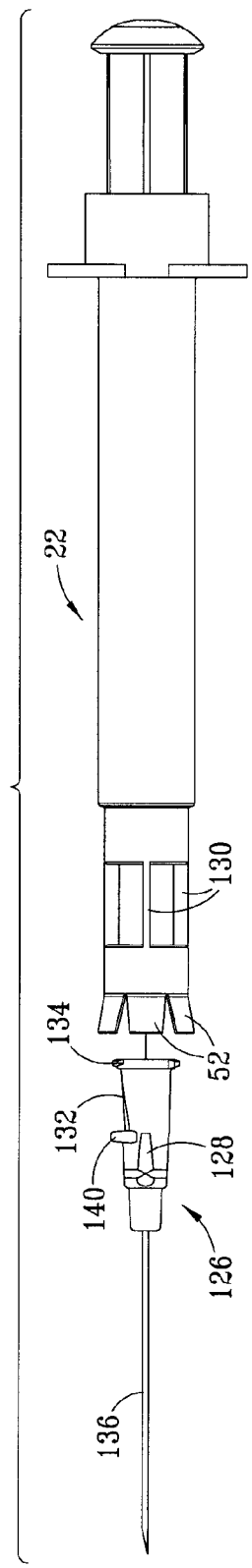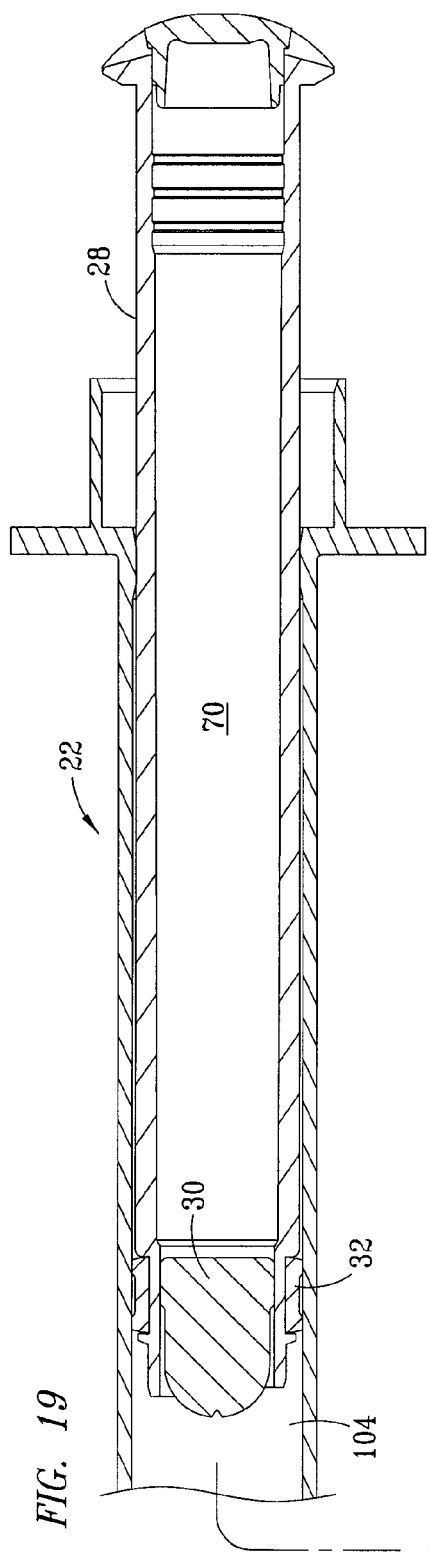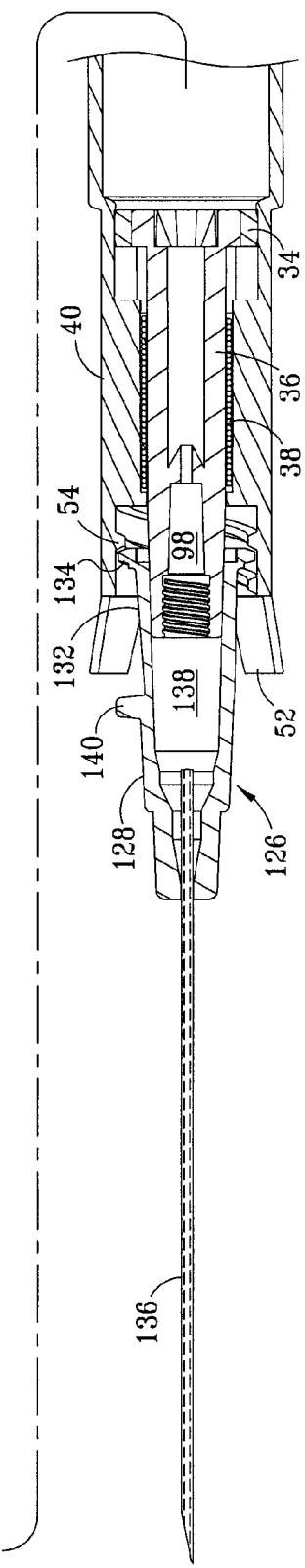
FIG. 18
FIG. 19

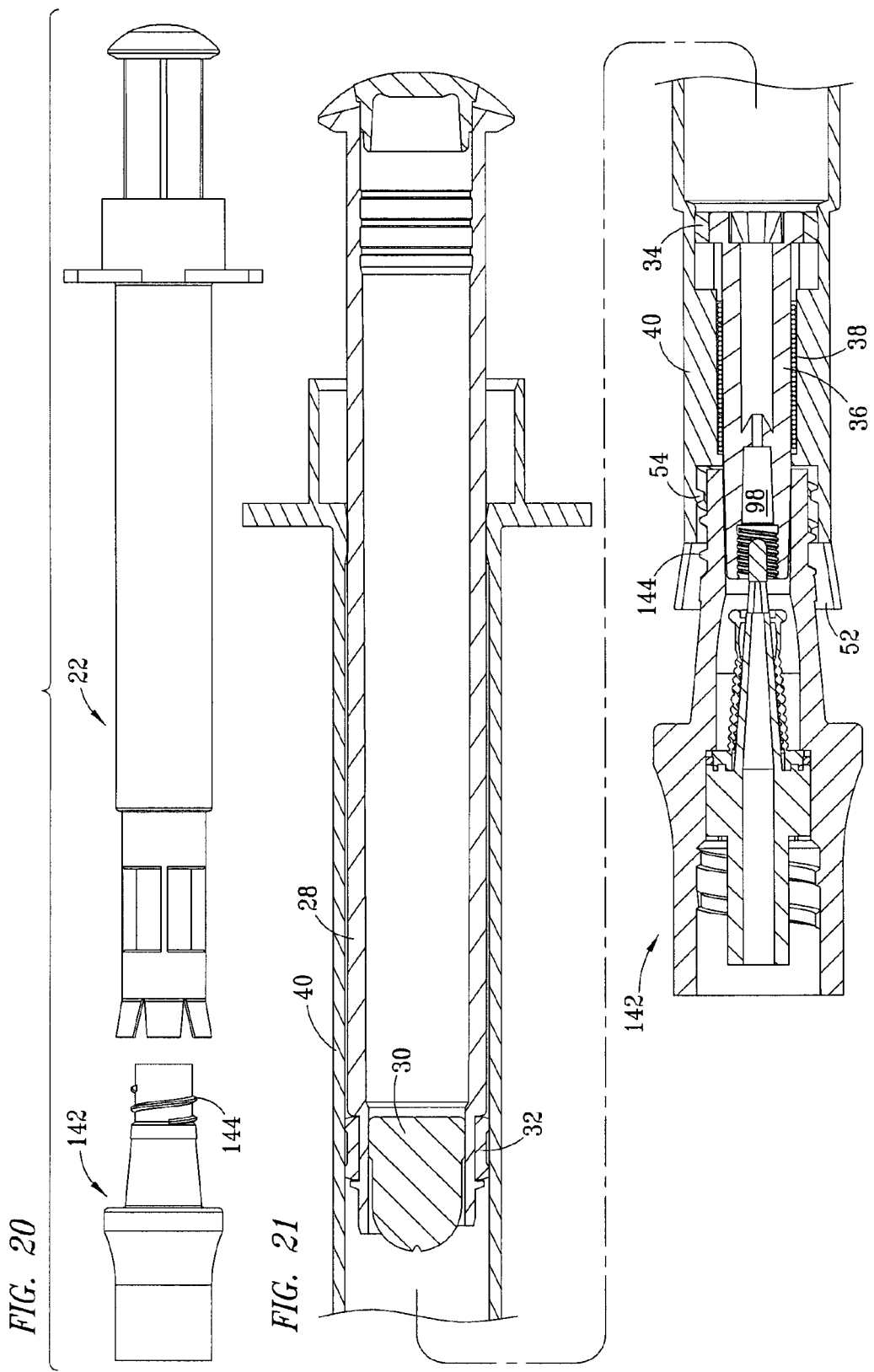

UNIVERSAL SYRINGE WITH RETRACTABLE NEEDLE

CROSS-REFERENCE TO RELATED APPLICATIONS

This application is a continuation of International Application Number PCT/US2009/059962, filed Oct. 8, 2009 and also claims the benefit of U.S. Provisional Application No. 61/107,578, filed Oct. 22, 2008.

BACKGROUND OF THE INVENTION

This invention relates to medical devices useful for infusion therapy and, more particularly, to a syringe that can be selectively used with a retractable needle, with a needle attached to a standard luer connector, or with other frontal attachment devices such as hubs, valves or other connectors suitable for use in needleless systems.

SUMMARY OF THE INVENTION

The apparatus of the invention is more widely applicable than known devices because it provides a user with the functionality of both a retractable needle and a needleless connector in a single syringe body. The subject apparatus preferably comprises a barrel, a plunger assembly slidably disposed inside the barrel, a needle retraction assembly and an optional protective guard disposed near the front of the barrel, a retraction cavity disposed inside the plunger assembly, and a closure sealing the forward end of the retraction cavity prior to retraction. When equipped with a needle assembly, which can be attached during manufacture or at the use site as desired, the apparatus can be used, for example, to draw medications from vials, to administer injections, and to infuse medications into IV delivery systems having pierceable ports. When used without a needle assembly, the apparatus is also attachable to a frontal attachment device such as a valve (e.g., CLAVE® connector) or luer hub for introducing medication into a closed IV delivery system. When used with a valve, the valve is desirably closed by activating the retraction mechanism prior to disengaging the valve from the syringe. The apparatus also desirably comprises a forwardly extending protective guard structure that helps protect the fluid pathway through the syringe from contamination due to incidental contact with a person or surface. The protective guard structure is preferably outwardly flared to facilitate movement of a needle assembly or other frontal attachment device into a position suitable for attachment to the syringe.

BRIEF DESCRIPTION OF THE DRAWINGS

The apparatus of the invention is further described and explained in relation to the following drawings wherein:

FIG. 1 is a rear perspective view of a preferred apparatus of the invention with an attached needle and needle cover;

FIG. 2 is an exploded front perspective view of the apparatus of FIG. 1;

FIG. 3 is a cross-sectional elevation view, partially broken away, of the apparatus of FIG. 1;

FIG. 4 is the cross-sectional elevation view of the apparatus of FIG. 3 with the needle cover removed;

FIG. 5 is a cross-sectional elevation view of the apparatus of FIG. 1 following removal of the needle cover and retraction of the needle into the syringe;

FIG. 6 is a cross-sectional side view of the plunger handle of FIG. 2;

FIG. 7 is an enlarged cross-sectional view of the forwardly extending tip of the plunger handle of FIG. 6;

FIG. 8 is an enlarged plan view of the needle holder of FIG. 2;

FIG. 9 is a cross-sectional view of the needle holder taken along line 9-9 of FIG. 8;

FIG. 10 is an enlarged cross-sectional view of the syringe barrel of FIG. 2;

FIG. 11 is an enlarged side view of the needle connector of FIG. 2;

FIG. 12 is a left end view of the needle connector of FIG. 11;

FIG. 13 is a cross-sectional view of the needle connector taken along line 13-13 of FIG. 12;

FIG. 14 is an enlarged side view of the needle assembly, comprising the needle connector, needle and needle cover of FIG. 2;

FIG. 15 is a cross-sectional view of the needle assembly of FIG. 14;

FIG. 16 is a cross-sectional detail view of the right end portion of the needle assembly of FIG. 15;

FIG. 17 is a cross-sectional view of the needle cover of FIG. 15 with the needle connector and needle removed;

FIG. 18 is a partially exploded side elevation view of a syringe as in FIG. 1, but having a frontal attachment that is a luer hub rather than a needle assembly as shown, for example, in FIGS. 2-4;

FIG. 19 is an enlarged cross-sectional view of the apparatus of FIG. 18, but showing the luer hub connected to the syringe;

FIG. 20 is a partially exploded side elevation view, partially broken away of a syringe as in FIG. 1, but having a frontal attachment that comprises a valve; and FIG. 21 is an enlarged cross-sectional view of the apparatus of FIG. 20, but showing the frontal attachment connected to the syringe.

DESCRIPTION OF PREFERRED EMBODIMENTS

Referring to FIG. 1, a preferred apparatus 20 of the invention is disclosed that comprises syringe 22 in combination with a frontal attachment that is needle assembly 24. Referring to FIG. 1 in combination with FIG. 2, an exploded view, syringe 22 of apparatus 20 preferably comprises a plunger assembly further comprising plunger handle 28, rear plug 26, front plug 30, and plunger seal 32. A retraction cavity is also disposed inside plunger handle 28 between front plug 30 and rear plug 26, and a portion of barrel 40 of syringe 22 can also serve as part of the retraction cavity. A vent 23 is desirably disposed near the rear of the plunger handle.

Syringe 22 also preferably comprises a retraction assembly further comprising needle holder 36, retainer member 34, and retraction spring 38. Retainer member 34 is preferably attachable to needle holder 36, and needle holder 36 is preferably partially insertable into spring 38. During the manufacture of syringe 22, the retraction assembly is preferably installed into barrel 40, and the plunger assembly is thereafter installed into barrel 40 behind the retraction assembly.

The needle assembly preferably comprises needle connector 42, needle 44 and needle cover 46. Needle 44 is preferably secured in fixed relation to needle connector 42, and the opposite end of needle connector 42 desirably threads into the cooperatively threaded forwardly extending portion of needle holder 36, as described below in relation to FIGS. 3 and 4. Apparatus 20 can be manufactured in this form if desired, or the needle assembly can be packaged and sold separately, and attached to syringe 22 at the use site.

Referring to FIGS. 3 and 4, retainer member 34 is preferably a separate, elastomeric member but can also be unitarily molded or otherwise formed as part of needle holder 36 to provide a fluid seal between it, needle holder 36 and barrel 40 and thereby establish a fluid chamber between needle the retraction assembly and plunger seal 32, and also hold spring 38 in compression by engagement with barrel 40. According to a particularly preferred embodiment of the invention, needle holder 36 comprises a slot or other structure that is engageable with a portion of barrel 40 to resist relative rotation between the needle holder and barrel, especially during attachment of the needle assembly or other frontal attachment to the syringe to form apparatus 20. The outside of needle cover 46 preferably slides inside of female threads 54 to permit threaded engagement between needle connector 42, to which needle 44 is attached in fixed relation by gluing or another similarly effective known method, and the cooperatively threaded portion of needle holder 36. The internal bore of needle 44 is thereby placed in fluid communication with internal bore 48 of needle holder 36 and with the fluid chamber behind needle holder 36 inside barrel 40. Front plug 30 inside the forwardly extending portion of plunger handle 28 prevents any fluid disposed inside the syringe from entering the portion of the retraction cavity inside the plunger handle prior to the time that front plug 30 is displaced rearwardly when retraction is initiated by the user. Elements of the protective guard structure 52 are desirably inclined outwardly relative to barrel 40 to reduce the likelihood of contaminating the forwardly extending tip of needle holder 36 prior to or during connection of the frontal attachment, in this case the needle assembly comprising needle cover 46, needle 40 and needle connector 42. The inclined elements of the protective guard structure 52 also assist in guiding the frontal attachment into alignment with the front of needle holder 36. Following attachment of needle connector 42 to needle holder 36, and just prior to use, needle cover 46 is desirably removed from frictional engagement with needle connector 42 as depicted in FIG. 4.

Referring to FIG. 5, following the infusion of fluid through syringe 22, needle connector 42 and needle 44, retraction of needle 44 is initiated by forcing plunger handle 28 forward relatively to barrel 40, thereby causing the front portion of front plug 30 to contact the rearwardly facing portion of needle holder 36. When this occurs, front plug 30 is displaced rearwardly and the forwardly extending tip of plunger handle 28 contacts and pushes retainer member 34 forwardly into annular recess 50, thereby disengaging retainer member 34 from needle holder 36 and allowing compressed spring 38 to force needle holder 36, needle connector 42 and needle 44 upwardly into syringe 22 to a position where the front tip of needle 44 no longer protrudes from the front of barrel 40 to a position where it could cause an accidental needlestick. When plunger handle 28 abuts against the inside of barrel 40, the pressure exerted against rear plug 26 by the hand of the user while simultaneously exerting an opposed finger force against the forwardly facing surface of radially extending flange member 64 desirably causes the peripheral member 66 around the back of plunger handle 28 to be forced into a recessed position inside the back opening of collar 62. As needle holder 36 moves rearwardly due to the force of spring 38, front plug 30 is also forced upwardly into the cavity inside plunger handle 28, and air inside the cavity can escape through vent 23.

Other portions of the preferred apparatus disclosed in relation to FIGS. 1-5 are further shown, described and explained in relation to FIGS. 6-17. FIG. 6 discloses plunger handle 28, retraction cavity 70 inside plunger handle 28, and a forwardly extending tip of plunger handle 28 that further comprises an annular projection 42 that cooperates with shoulder 76 to define a recess 74 into which plunger seal 32 described above can be seated to provide a fluid seal against the inside of the syringe barrel. Arrow 78 indicates the open front end of plunger handle 78 in which front plug 30 of FIG. 2 is seated during assembly. Referring to FIG. 7, a detail view is shown that better depicts the stepped front end of plunger handle 28 in which surface 80 projects forwardly to a greater extent than surface 82. Such a step is preferred for concentrating the retraction force applied through the plunger handle against one side of retainer member 34 prior to the other side, thereby assisting in the removal of retainer member 34 from needle holder 36.

FIG. 8 further depicts cylindrical head 84, split annular shoulder 86, slot 90, slot walls 88, 92, and tapered outside luer surface 58 of needle holder 36. The rear of spring 38, discussed above, abuts against shoulder 86, and the outer diameter of the forwardly extending portion of needle holder 36 is desirably slightly less than the inside diameter of compressed spring 38 to allow the coils of spring 38 to encircle the forwardly extending part of the needle holder. Referring to FIG. 9, female threads 92 inside the portion comprising luer surface 58 are desirably cooperatively sized and aligned to receive the corresponding male threads of needle connector 42, described above, into engagement therewith. Tapered surface 100 desirably slidably engages surface 112 of needle connector 42, described in relation to FIGS. 11 and 12 below, and passageways 94, 96 and 98 cooperate to establish a fluid flow path through needle holder 36.

FIG. 10 further discloses rear opening 60, annular collar 62, grippable finger flanges 64, female threads 54 and forwardly and outwardly projecting elements of the protective guard structure 52.

FIGS. 11-13 further disclose circumferentially disposed ribs 108 around the front portion of needle connector 42, centrally disposed bore 106 establishing a fluid pathway through the connector, male threads 110, and tapered guiding and engagement surface 112.

FIGS. 14-17 further disclose rear end 116 and rear opening 122, forwardly extending tapered outside wall section 114, and closed end 115 of needle cover 46. Prior to attachment of needle connector 42 to syringe 22, discussed above, the rear end of needle 44 is desirably inserted into elongate cavity 118 of needle cover 46, and is glued or otherwise attached in fixed relation to needle connector 42 inside bore 106. Needle connector 42 desirably frictionally engages the inside wall of section 116 of needle cover 46 in such manner that the free end of needle connector 42 resides inside substantially cylindrical space 120, most preferably packaged inside a sterile wrapper if provided as a separate assembly, until the time when needle connector 42 is threaded into the needle holder of a syringe as described above.

FIGS. 18-19 disclose a frontal attachment 126 comprising luer hub 132, luer locking flange 134, needle 136 and finger grips 128, 140 for use in threading the luer hub into sealing engagement with female threads 54 inside the front portion of barrel 40 of syringe 122, behind protective guard structure 52. Grippable surface ridges 130 are also desirably provided on syringe 22 to facilitate gripping during connection of the frontal attachment. Internal cavity 138 of frontal attachment 126 provides fluid communication between needle 136 and cavity 98 inside needle connector 42 as discussed above. Although the retraction assembly comprising retainer member 34, needle holder 36 and spring 38 are still in place, needle 136 cannot be retracted inside syringe 22 in this embodiment, and must be recovered or, more preferably, disposed in an approved sharps disposal container.

FIGS. 20-21 disclose a frontal attachment 142 that is a valve assembly having external threads 144 that is also attachable to female threads 54 behind protective guard structure 52 of barrel 40. In this embodiment, there is no needle to be retracted following use.

Other alterations and modifications of the invention will likewise become apparent to those of ordinary skill in the art upon reading this specification in view of the accompanying drawings, and it is intended that the scope of the invention disclosed herein be limited only by the broadest interpretation of the appended claims to which the inventor is legally entitled.

I claim:

1. A syringe for medical use, the syringe comprising a barrel, a retraction assembly seated in a front portion of the barrel after being inserted through an opening in the rear of the barrel, a protective guard structure disposed near the front of the barrel, and a plunger assembly slidably engaging an inside wall of the barrel behind the retraction assembly, wherein the syringe is configured to be directly attachable to a frontal attachment selected from the group consisting of a retractable needle connector, a luer hub with a non-retractable needle, and a valve assembly;

wherein the retraction assembly comprises a needle holder, retainer member and compressed retraction spring; and wherein the guard structure comprises a plurality of spaced-apart elements having free distal ends that extend forwardly past any other part of the barrel or retraction assembly.

2. The syringe of claim 1 wherein the free distal ends of the spaced-apart elements of the guard structure are outwardly inclined.

* * * * *